United States Patent
Lautenschläger

(12) 
(10) Patent No.: US 10,687,774 B2
(45) Date of Patent: Jun. 23, 2020

(54) METHOD AND APPARATUS FOR VISUALIZING A BLOOD VESSEL

(71) Applicant: Stefan Lautenschläger, Nürnberg (DE)

(72) Inventor: Stefan Lautenschläger, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 469 days.

(21) Appl. No.: 14/658,175

(22) Filed: Mar. 14, 2015

(65) Prior Publication Data

US 2015/0257724 A1    Sep. 17, 2015

(30) Foreign Application Priority Data

Mar. 14, 2014   (DE) .......................... 10 2014 204 799

(51) Int. Cl.
*A61B 6/00* (2006.01)

(52) U.S. Cl.
CPC .............. *A61B 6/504* (2013.01); *A61B 6/481* (2013.01); *A61B 6/487* (2013.01); *A61B 6/5217* (2013.01); *A61B 6/5235* (2013.01); *A61B 6/4441* (2013.01); *A61B 6/482* (2013.01)

(58) Field of Classification Search
None
See application file for complete search history.

(56) References Cited

U.S. PATENT DOCUMENTS

| 6,185,271 | B1 | 2/2001 | Kinsinger | |
| 2004/0101104 | A1* | 5/2004 | Avinash | A61B 6/032 |
| | | | | 378/98.12 |
| 2007/0189443 | A1 | 8/2007 | Walter et al. | |
| 2011/0182492 | A1* | 7/2011 | Grass | A61B 6/4441 |
| | | | | 382/131 |

(Continued)

FOREIGN PATENT DOCUMENTS

| CN | 1518955 A | 8/2004 |
| CN | 103619237 A | 3/2014 |
| DE | 102010022526 A1 | 10/2011 |

OTHER PUBLICATIONS

Ruijters et al. "Real-Time Integration of 3-D Multimodality Data in Interventional Neuroangiography" Journal of Electronic Imaging 18(3), Jul.-Sep. 2009 pp. 033014-(1-7).*

(Continued)

*Primary Examiner* — Angela M Hoffa
*Assistant Examiner* — Farouk A Bruce
(74) *Attorney, Agent, or Firm* — Lempia Summerfield Katz LLC

(57) ABSTRACT

A method for representing a blood vessel including a thrombosed section of the blood vessel in a patient is provided. The method includes capturing a first volume data set after administration of a contrast agent, locating a proximal and/or distal end of the thrombosed section of the blood vessel with the aid of the first volume data set, and defining a data capture area for a second volume data set based on the proximal and/or distal end of the thrombosed section of the (Continued)

blood vessel that has been located. The method also includes capturing the second volume data set, segmenting the thrombosed section of the blood vessel from the second volume data set, capturing fluoroscopic images, and superimposing the segmented thrombosed section of the blood vessel with the fluoroscopic images.

14 Claims, 2 Drawing Sheets

(56) References Cited

U.S. PATENT DOCUMENTS

2011/0201915 A1* 8/2011 Gogin .................. A61B 5/0456
                                                        600/407
2014/0313196 A1    10/2014 Mistretta et al.

OTHER PUBLICATIONS

Kolditz et al. "Volume-of-interest (VOI) imaging in C-arm flat-detector CT for high image quality at reduced Dose" Medical Physics 37 (6), Jun. 2010 pp. 2719-2730.*
Chinese Office Action for Chinese Patent Application No. 201510172183 dated Mar. 3, 2017, with English translation.
German Office Action for German Application No. 10 2014 204 799.4, dated Nov. 17, 2014, with English Translation.
Kolditz D. et al.: "Volume-of-interest (VOI) imaging in C-arm flat-detector CT for high image quality at reduced dose," Medical Physics, vol. 37, No. 6, pp. 2719-2730, 2010.

* cited by examiner

METHOD AND APPARATUS FOR VISUALIZING A BLOOD VESSEL

This application claims the benefit of DE 10 2014 204 799.4, filed on Mar. 14, 2014, which is hereby incorporated by reference in its entirety.

BACKGROUND

The present embodiments relate to a method and an apparatus for representing a blood vessel including a thrombosed section of a blood vessel of a patient.

A thrombosis is a vascular disease in which a blood clot (e.g., thrombus) forms in a blood vessel and partially or completely obstructs the blood vessel. Thrombi may appear in any blood vessel. In ischemic stroke, which is the most common form of stroke, a thrombus obstructs an artery. The thrombus leads to reduced perfusion of the supply area located at the distal end.

To treat vascular diseases (e.g., thrombosis), it is a known procedure to insert a mini-catheter into the patient's vascular system in order to dissolve or remove the thrombus. A current method is "mechanical thrombectomy" using a "stent retriever". This involves guiding the stent retriever through the thrombus and inserting a mesh (e.g., similar to a stent) along the length of the thrombus. After a short time (e.g., about 5 minutes), the wires of the stent retriever have become entwined with the thrombus, and the stent retriever may be extracted from the vessel together with the thrombus that is caught up therein.

In the procedure described above, the challenge is to grasp hold of the entire thrombus with the stent retriever mesh. If this is unsuccessful and only part of the thrombus is removed, fragments of the thrombus may be deported to other branches of the vascular system distal to the original position of the thrombus. This may lead to considerable negative effects (e.g., to a further obstruction in the distal vascular area). It is therefore important for the physician treating the patient to know the position and the length of the thrombus so that the physician may: a) navigate safely and reliably through the thrombus (without perforating the vessel); and b) push the distal end of the stent retriever far enough forward for the stent retriever to reliably grasp hold of the entire thrombus.

A known method for visualizing the vascular structure is digital subtraction angiography (DSA), in which a contrasted X-ray image (e.g., X-ray image after administration of a contrast agent) is subtracted from a native image (e.g., mask image, image without administration of contrast agent). Thus, the resulting image then contains only the blood vessels marked with contrast agent, with at least extensive blanking out of the background (e.g., soft tissues, bone). If the thrombus is located in an artery, the contrast agent is supplied arterially, for example. Due to the vascular obstruction by the thrombus, however, the contrast agent stops at the proximal end of the thrombus, such that it may not be possible to determine the position and length of the thrombus. The physician consequently lacks information on the vascular course of the artery in the area around the thrombus and also on the overall length of the thrombus.

A partial solution to this problem may be achieved by carrying out 3D scans (e.g., volume scans) involving intravenous administration of contrast agent. If the waiting period between the administration of contrast agent and the acquisition of the 3D scan is sufficiently long and the collateral supply to the obstructed vascular segment is at least adequate, the thrombosed vessel fills up in a retrograde manner (e.g., backwards) and consequently indicates the distal end of the thrombus to the physician. Thus, the positions of the proximal end and the distal end of the thrombus are therefore known to the physician. However, this procedure is comparatively expensive and time-consuming.

Even when all the parameters of this both technically and "practically" complex scan (e.g., contrast agent protocol, timing, collateral blood supply, type of reconstruction) have been successful, the following data is still incomplete or not available: a) Vascular course of the thrombosed vessel; only the proximal and distal ends of the thrombus are known.

Within the thrombus, the physician has to navigate "blind", however, so that there is a high risk of vascular injury (e.g., of perforation). The following data also is still incompletely or not available: b) Length of the thrombus; depending on the course of the vessel (e.g., straight or curved) between the known fixed points (e.g., proximal and distal end of the thrombus), there are different lengths of thrombus. Since the thrombectomy device to be used (e.g., a stent retriever) may be aligned as much as possible with the length of the thrombus, the image does not make the physician aware of the optimum length of the device to be used. Too short a stent retriever leads to the aforementioned problems. An unnecessarily long stent retriever leads to increased difficulties in navigating through the vascular system and consequently increases the risk of vascular injury.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method and an apparatus for representing a blood vessel that allow the imaging of an obstructed section of a blood vessel and allow imaging of an obstructed section of a blood vessel in as simple a manner as possible with minimal exposure to radiation are provided.

The method according to one or more of the present embodiments includes capturing a first, contrasted volume data set (e.g., image after administration of contrast agent), and locating a proximal and/or distal end of a thrombosed section of the blood vessel with the aid of the first volume data set. A data capture area is defined for a second volume data set based on the proximal and/or distal end of the thrombosed section of the blood vessel. The second volume data set is captured, and the thrombosed section of the blood vessel is segmented from the second volume data set. Fluoroscopic images are captured, and the segmented, thrombosed section of the blood vessel is superimposed with the fluoroscopic images.

The apparatus according to one or more of the present embodiments is suited and equipped to carry out the method and encompasses a data capture device to capture volume data sets and fluoroscopic images, and a control and computation device. The control and computation device is configured to control the data capture device, to segment a thrombosed section of the blood vessel out of a volume data set, and to superimpose the thrombosed section of the blood vessel with the fluoroscopic images.

According to one or more of the present embodiments, a first image data set relating to an area of interest in the human or animal body is captured. The image is a volume data set (e.g., 3D scan). This may be achieved by, for example, computed tomography (CT), magnetic resonance tomography (MRT) or by C-arc-based imaging (e.g., capture of a C-arm CT data set). The data capture is achieved after administration of contrast agent in order to obtain a good image of the vascular system. Data capture may be achieved after intra-arterial administration of contrast agent, although an intravenous administration of contrast agent may also be provided. The first volume data set includes an image of the blood vessel of interest in which the thrombus is located. In other words, the first volume data set contains an image of the blood vessel up to the proximal end of the thrombus and/or from the distal end of the thrombus. The thrombus (e.g., the obstructed section of the blood vessel) may not be contrasted by the contrast agent in this first volume data set and is therefore not visible or is barely visible.

In another act, the "point of interruption in the vessel" (e.g., the proximal end of the thrombus) or with intravenous administration of contrast agent, the distal end of the thrombus is located. A determination of the position of the proximal and/or distal end of the thrombus thus ensues. This may be done manually on a screen using, for example, a computer input device, or automatically by an image processing system (e.g., computation device).

In another act, a data capture area for the acquisition of a further image data set is designated. The data capture area is smaller than the data capture area for the first volume data set. The second volume data set therefore includes only an extract from the spatial area covered by the first volume data set. The purpose of this procedure includes minimizing the patient's exposure to X-rays through this second data capture. The data capture area for the second volume data set is selected so as to provide that the entire area around the thrombosed section of the blood vessel (e.g., the entire thrombus) is included. For this purpose, the data capture area may be selected such that the size thereof is essentially determined from the length of the expected thrombus. For example, provision may be made for size definition (e.g., a diameter or a length) of the data capture area to be selected such that this is essentially (e.g., over 50%) determined by the length of the expected thrombus. The data capture area is therefore placed in a targeted manner in or around the area of the thrombus.

In another act, the acquisition of the second volume data set ensues. This may be achieved by, for example, computed tomography (CT), magnetic resonance tomography (MRT) or by C-arc-based imaging (e.g., capture of a further C-arm CT data set). The capture of the second image data set therefore ensues in a targeted manner in the previously defined data capture area, which contains the thrombus. The capture of the second image data set therefore ensues in a targeted manner in the area of the thrombus (e.g., within an area with a volume that is smaller than the volume of the area for the first image data set). In a targeted manner, it is therefore only the area of the thrombus that is irradiated or captured. For this purpose, the patient may be re-centered accordingly (e.g., arranged in the isocenter of the imaging device). A corresponding collimation is carried out. Alternatively, an asymmetrical collimation may be carried out during the acquisition of the 3D image, which renders the repositioning of the patient unnecessary. In the second volume data set, the entire vessel including the thrombosed section (e.g., obstructed section) of the vessel is visible. The image data set therefore contains an image of the course of the blood vessel in the area of the thrombus. For this purpose, there ensues an appropriate selection of the imaging and/or display parameters through which a good contrast may likewise be achieved in the area of the thrombosed section of the blood vessel. The imaging may not be based on contrasting achieved with a contrast agent, which would not show the obstructed section of the blood vessel that is desired. For representing the thrombus, "Dual Energy Imaging", for example, may be selected. This is a procedure that is basically known and makes it possible to differentiate between different materials. The procedure involves irradiating the areas of interest with different energies (e.g., X-ray beam energies). Because the data capture area is restricted to the direct surroundings of the thrombosed section of the blood vessel, the patient's exposure to radiation may be minimized.

The thrombosed section of the blood vessel (e.g., optionally including a point of transition to the healthy section of the blood vessel) is then segmented (e.g., separated from the surrounding structures). The process acts described in the aforementioned (e.g., the capture of the first and optionally also the capture of the second image data set) may be carried out pre-interventionally (e.g., chronologically prior to a treatment of the patient).

During the treatment, a series of image data sets are captured consecutively. The series of image data sets serve, for example, to simplify navigation within the vascular system for the physician through a visual image of the vascular system. These "interventional fluoroscopic images" may also be referred to as live images. These may be spatially two-dimensional images. Even better orientation may generate a chronological sequence of volume data sets. The fluoroscopic images may be captured as non-contrasted images (e.g., without contrasting using a contrast agent) and show, for example, the intervention instrument (e.g., the stent retriever).

In order to allow a guided, reliable, and safe passage of the microcatheter or stent retriever through the thrombus, the segmented thrombus is superimposed on the live images. A representation of the superimposed image is provided on a display device (e.g., screen, monitor).

With the representation method according to one or more of the present embodiments, a thrombectomy may be achieved in a particularly safe and reliable manner.

The capture of the second volume data set and segmentation of the thrombosed section of the blood vessel may also be carried out during an intervention. After a treatment has been carried out (e.g., after the removal of the thrombus), a further image data set may optionally be captured in a similar manner to the capture of the second image data set in order, where necessary, to detect any remaining thrombus fragments.

The live images themselves may contain an image of the blood vessel or vascular trees and optionally be superimposed for this purpose with a previously captured image of the vascular tree (e.g., the first volume data set). One aspect of the method according to one or more of the present embodiments may consequently be seen in the superimposition of the first volume data set, of the thrombus segmented from the second volume data set, and of the fluoroscopic images. The first volume data set represents a vascular system contrasted with contrast agent (e.g., without the thrombus), and the fluoroscopic images, with temporal resolution, represent the intervention instrument.

In one embodiment of the method, the second volume data set is captured with different energies (e.g., X-ray energies; dual-energy method). This may be provided, for example, by changing an X-ray tube or by using different voltages on the two levels of a biplanar unit. The different voltages and/or energies are adapted or optimized to the typical composition of a thrombus. The use of different X-ray energies allows the representation of the thrombosed section of the blood vessel (e.g., without using a contrast agent). Dual-energy methods are basically known in the prior art and are therefore not explained in greater detail hereinafter. Blood flowing through the different X-ray energies may be distinguished from coagulated blood such that the thrombus may be made visible. The thrombus may be separated from the surrounding structures by analyzing the captured data (e.g., 3D segmentation).

Accordingly, the second volume data set may be a non-contrasted volume data set. In this way, the patient is not exposed to additional contrast agent through this additional scan, so that the method is advantageous, for example, with respect to "multimorbid" patients (e.g., with kidney problems, etc.). Restriction to the direct area or to the direct surroundings of the thrombus provides that exposure to radiation is reduced. The locating of the thrombus in the patient's vascular system is provided with the preceding first scan (e.g., first volume data set), which may be required anyway for imaging the vascular system.

In one embodiment, the data capture area for the second volume data set is defined through the definition of a midpoint of the data capture area. In other words, a midpoint that forms the midpoint of the data capture area is designated. This midpoint may be set in the area of the thrombosed section of the blood vessel, at, for example, the proximal or distal end of the thrombosed section of the blood vessel or in an area between the proximal end and the distal end. The proximal end and/or the distal end of the thrombus is determined by the first image data set. In the first image data set, the proximal end and/or the distal end of the thrombus may be recognized particularly well due to contrasting with contrast agent.

In a further embodiment, the data capture area for the second volume data set is defined as a spherical volume with a predetermined radius or diameter. For this purpose, a midpoint of the spherical volume or virtual ball may be defined using an image processing system (e.g., at the proximal end or the distal end of the thrombus or between the proximal end and the distal end). A radius of the spherical volume is defined. The radius is selected such that the entire thrombus is safely located within the spherical volume, irrespective of the position of the midpoint. For this purpose, a maximum thrombus length is assumed based on empirical data, and a predetermined safety margin is added. Assuming a maximum thrombus length of 16 mm and a safety margin of 4 mm, the result is, for example, a radius of 20 mm if the midpoint is set at the proximal or distal end of the thrombus.

If, for example, due to the intravenous administration of contrast agent, both the proximal and the distal end of the thrombus are known, the midpoint of the virtual ball may be set in an area between the proximal end and the distal end of the thrombus (e.g., in the center). In this way, the data capture area for the second volume data set may be reduced. In the present scenario, for example, the radius of the spherical volume may be selected as half the distance between the proximal end and the distal end of the thrombus plus the safety margin.

The capture of the second volume data set may be provided in a targeted manner in the defined data capture area. This is to be understood, for example, as providing that the X-ray beams are directed in a targeted manner at the second data capture area, such that adjacent areas (e.g., along the longitudinal axis of the patient) are hardly exposed or not exposed to radiation. The isocenter of the imaging device (e.g., irradiation device, X-ray device) may be set in the midpoint of the data capture area. Restricting the irradiated area in the acquisition of the 3D scan to the virtual ball provides that exposure to radiation is extremely low.

In a further embodiment of the method, the length and/or the course of the thrombosed section of the blood vessel are determined from the second volume data set. Not only an image of the thrombosed section of the blood vessel is provided, but a calculation of the dimension or of the spatial extent of the thrombus is also provided. An appropriate device (e.g., a processor) may be used to calculate the dimension or of the spatial extent of the thrombus from the data in the second volume data set.

An intervention device may be designated for treating the thrombosed section of the blood vessel based on the length and/or the course of the thrombosed section of the blood vessel that has/have been determined. Knowledge of the length and/or the course of the thrombus may also make it possible to determine what length of intervention device (e.g., of a stent retriever) is to be used for treating the thrombosis. The length of the intervention device may correspond with the length of the thrombus plus a predetermined safety margin. In this way, an optimum length of the stent retriever may be designated.

In a further embodiment of the method, the segmented, thrombosed section of the blood vessel is superimposed with the first volume data set or with a projected image reconstructed therefrom. In this way, the entire course of the blood vessel becomes visible, including the course of the thrombus.

The advantages described with respect to the method may be achieved using the apparatus.

DETAILED DESCRIPTION

Figure 1:
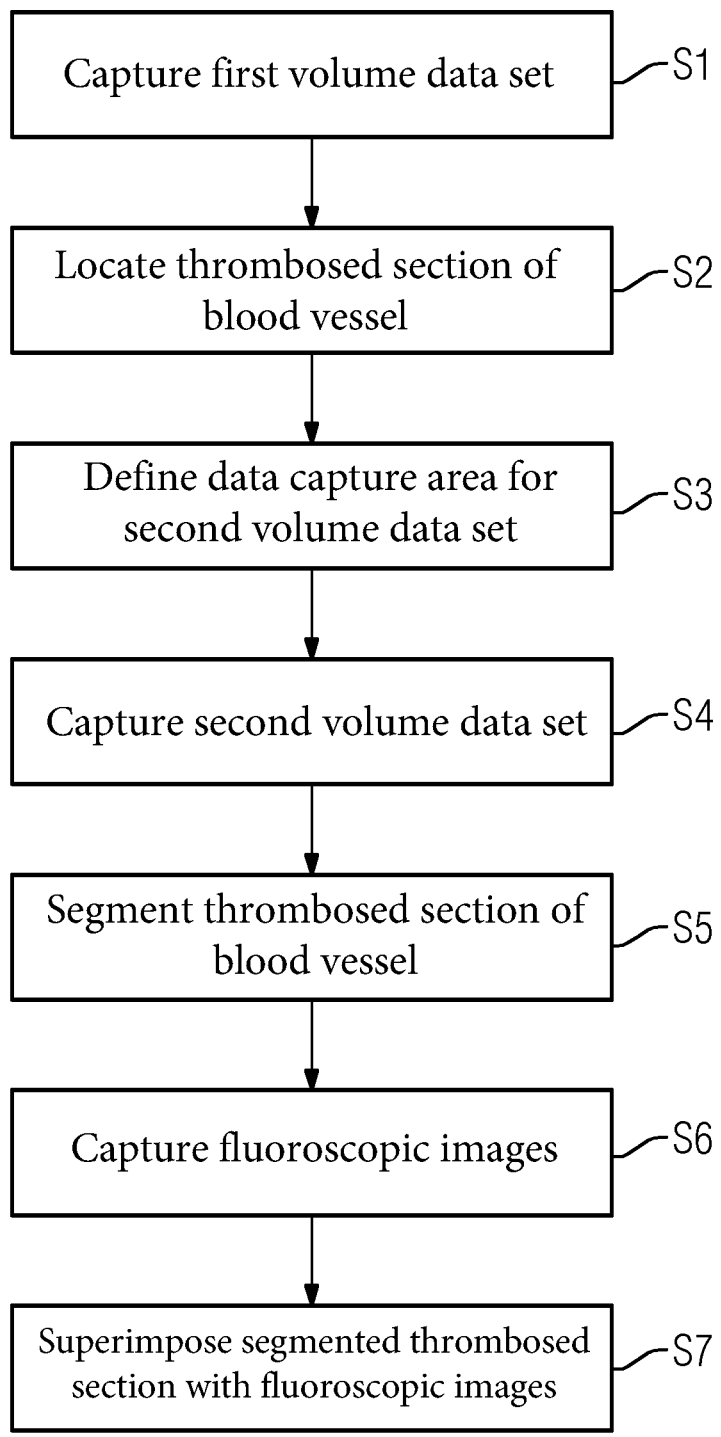
FIG. 1 shows a flow diagram to represent process acts of an embodiment of a method.

The individual process acts according to an embodiment of the method are described hereinafter with the aid of FIG. 1.

In act S1 (e.g., capture of a first volume data set), a first volume data set (e.g., image data set) is first acquired (e.g., pre-interventionally). The first volume data set is used to represent a "map" of the vascular system. For this purpose, a medical acquisition device (e.g., a computer tomograph, a magnetic resonance device or a C-arm device) may be used. Contrasted projected images are captured from different projection directions and reconstructed with an image reconstruction into a spatially three-dimensional volume data set, in a basically known manner. In the volume data set, the vessels may be recognized particularly well due to the contrasting using contrast agent. The imaging may ensue using the principle of digital subtraction angiography (e.g., a "native image" is subtracted from the contrast agent-contrasted X-ray image).

Using the first volume data set with the blood vessels marked with contrast agent, in act S2 (e.g., locating the thrombosed section of the blood vessel), either manually or using an image recognition algorithm, a vascular block (e.g., vascular obstruction, stenosis, thrombus) is located. Due to the contrasting achieved with a contrast agent, this is reliable and is simple to carry out. The locating of the thrombosed section of the blood vessel relates, for example, to the proximal or distal end of the obstruction (e.g., of the thrombus).

From the position of the thrombus, in act S3 (e.g., definition of a data capture area for a second volume data set), a second data capture area (e.g., to capture a second volume data set) is defined. The second data capture area is smaller in size than the first data capture area used to capture the first volume data set. The second data capture area contains the entire thrombosed section of the blood vessel. For this purpose, a midpoint of the second data capture area is set in the area of the thrombosed section of the blood vessel and, based on empirical data, regarding a maximum length of the thrombosed section of the blood vessel, a radius (or diameter) of the data capture area is defined.

In act S4 (e.g., capture of the second volume data set), capture of the second volume data set ensues. This may, for example, be carried out before, but optionally also during, an intervention. Imaging ensues with different X-ray energies that allow representation of the thrombus (e.g., without contrasting achieved with a contrast agent).

In act step S5 (e.g., segmentation of the thrombosed section of the blood vessel), the thrombosed section of the blood vessel represented in the second volume data set is segmented out therefrom. The segmentation may ensue using basically known methods (e.g., threshold value-based).

During the intervention, a series of fluoroscopic images are captured (act S6, capture of fluoroscopic images). The fluoroscopic images are captured in a rapid chronological sequence, such that a kind of film is produced. The fluoroscopic images contain an image of the intervention instrument and, in order to represent the course of the vessel, the fluoroscopic images may be superimposed with corresponding back projections from the first volume data set. Other techniques, however, are also possible for representing the course of the vessel in the fluoroscopic images. The fluoroscopic images may be captured when contrast agent has been administered.

In act S7 (e.g., superimposition of the segmented, thrombosed section of the blood vessel with the fluoroscopic images), the segmented, thrombosed section of the blood vessel is superimposed with the interventional fluoroscopic images (e.g., live images). In this way, an image of the obstructed section of the blood vessel (e.g., the section not included in the original fluoroscopic images) appears in the fluoroscopic images. The physician may consequently negotiate safely through the thrombus, since the physician is able to detect the precise position and length of the thrombus in the superimposed images. For this purpose, the superimposed images may be represented on a display apparatus (e.g., screen). The fluoroscopic images may be captured using a C-arm device.

Figure 2:
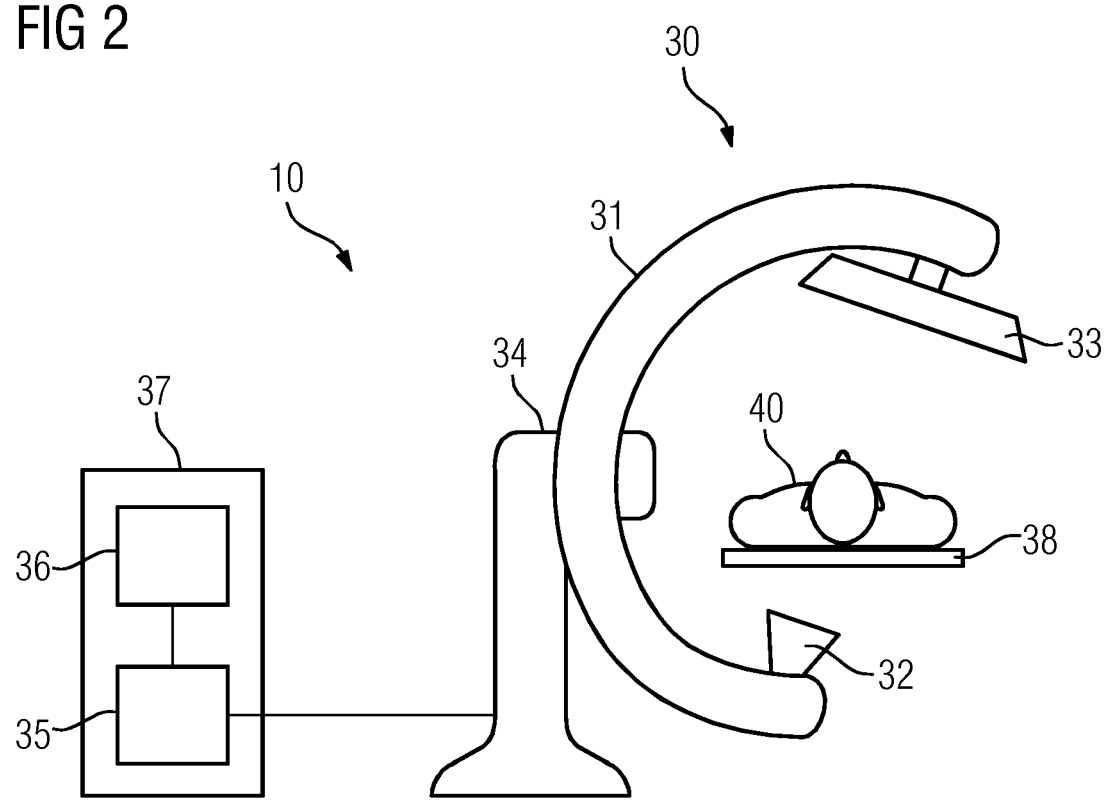
FIG. 2 shows an apparatus for carrying out the method according to the invention.

FIG. 2 shows an embodiment of an apparatus 10, with which, for example, the method according to one or more of the present embodiments may be carried out. The apparatus includes an imaging device 30 (e.g., an X-ray device; a C-arm device). The imaging device 30 includes an X-ray source 32 and an X-ray detector 33 that are mounted on arms of the C-arm 31. The C-arm 31 is rotatable round a patient couch 38. The X-ray detector 33 may be a digital detector that may generate digital X-ray images of a patient 40 who is lying on the patient couch 38. The C-arm is movably mounted on a stand 34.

The movements of the C-arm and the acquisition of X-ray images are controlled by a control and computation device 35. The digital X-ray images acquired by the X-ray detector 33 may be transmitted to the control and computation device 35 and processed therein. The control and computation device 35 accesses a memory 36, which is suitable or configured for storing X-ray images. The control and computation device 35 and the memory 36 may be part of a computer 37, which is, for example, a PC, a workstation or a console for the imaging device 30. A screen to display X-ray images and input devices such as a keypad and/or a mouse may also be present.

The imaging device 30 is suited and equipped to capture volume data sets and to capture time series images (e.g., fluoroscopic images). In this way, all the data sets in the method according to one or more of the present embodiments (e.g., first and second volume data set and fluoroscopic images) may be captured with one and the same device (e.g., without moving the patient anywhere). The control and computation device 35 is equipped to segment a thrombosed section of the blood vessel from a volume data set and superimpose the segmented, thrombosed section of the blood vessel with the fluoroscopic images. The control and computation device 35 may be further equipped to detect the thrombosed section of the blood vessel (e.g., thrombus) in the second volume data set and mark the proximal and/or distal end of the thrombus.

Although the invention has been illustrated and described in greater detail with embodiments, the invention is not restricted to the examples disclosed. Other variants may be derived therefrom by a person skilled in the art, without going beyond the scope of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for visualizing a blood vessel of a patient during an intervention, the blood vessel including a thrombosed section, the method comprising:
capturing, by an imaging device after administration of a contrast agent, a first contrasted volume data set;
locating a proximal end and a distal end of the thrombosed section of the blood vessel within the first contrasted volume data set;
defining a data capture region area for a second volume data set based on the located proximal end and the located distal end of the thrombosed section of the blood vessel that has been located within the first contrasted volume data set such that the data capture region for the second volume data set includes only an extract of a spatial region covered by the first contrasted volume data set;
capturing, by the imaging device, the second volume data set, wherein capturing the second volume data set is limited to the data capture region defined based on the located proximal end and the located distal end of the thrombosed section of the blood vessel;

segmenting the thrombosed section of the blood vessel out of the second volume data set;

capturing, after the second volume data set is captured, live fluoroscopic images during the intervention; and superimposing the segmented thrombosed section of the blood vessel with the live fluoroscopic images, wherein superimposing comprises displaying, by a display, an image of the segmented thrombosed section of the blood vessel not otherwise shown in the live fluoroscopic images, the image of the segmented thrombosed section of the blood vessel being based on a three-dimensional image of the data capture region reconstructed using projection images from only the second volume data set.

2. The method of claim 1, wherein the second volume data set is captured using different energies.

3. The method of claim 1, wherein the second volume data set is a non-contrasted volume data set.

4. The method of claim 1, wherein defining the data capture region for the second volume data set further comprises defining a mid-point in the data capture region, the mid-point being set in a region of the thrombosed section of the blood vessel.

5. The method of claim 1, wherein the data capture region for the second volume data set is defined as a spherical region area with a predetermined radius.

6. The method of claim 1, wherein capturing the second volume data set comprises capturing the second volume data set in a targeted manner in the defined data capture region.

7. The method of claim 1, wherein a length, a course, or the length and the course of the thrombosed section of the blood vessel are determined from the second volume data set.

8. The method of claim 7, wherein an intervention device for treating the thrombosed section of the blood vessel is designated based on the length, the course, or the
length and the course of the thrombosed section of the blood vessel that have been determined.

9. The method of claim 1, wherein the segmented, thrombosed section of the blood vessel is superimposed with the first volume data set or with a projected image reconstructed therefrom.

10. An apparatus for representing a blood vessel including a thrombosed section of the blood vessel in a patient during an intervention, a proximal end and a distal end of the thrombosed section of the blood vessel in the patient being located with the aid of a first contrasted volume data set, the apparatus comprising:

a data capture device operable to capture a first contrasted volume data set, a second volume data set limited to a data capture region defined based on the located proximal end and the located distal end of the thrombosed section of the blood vessel, and live fluoroscopic images, the live fluoroscopic images being captured after the second volume data set;

a control and computation device configured to control the data capture device to:

define the data capture region for the second volume data set based on the located proximal end and the located distal end of a thrombosed section of the blood vessel that has been located within the first contrasted volume data set such that the data capture region for the second volume data set includes only an extract of a spatial region area covered by the first contrasted volume data set;

segment the thrombosed section of the blood vessel out of the second volume data set; and superimpose the segmented thrombosed section of the blood vessel with the live fluoroscopic images; and a display device configured to display an image of the superimposed segmented thrombosed section of the blood vessel not otherwise shown in the live fluoroscopic images, the image of the superimposed segmented thrombosed section of the blood vessel being based on a three-dimensional image of the data capture region reconstructed using projection images from only the second volume data set.

11. The apparatus of claim 10, wherein the second volume data set is captured using different energies.

12. The apparatus of claim 10, wherein the second volume data set is a non-contrasted volume data set.

13. The apparatus of claim 10, wherein the data capture region for the second volume data set is defined as a spherical region with a predetermined radius.

14. The apparatus of claim 10, wherein the control and computation device is further configured to determine a length, a course, or the length and the course of the thrombosed section of the blood vessel from the second volume data set.

* * * * *